United States Patent [19]

Ozel

[11] Patent Number: 5,135,745
[45] Date of Patent: Aug. 4, 1992

[54] EXTRACTS OF NERIUM SPECIES, METHODS OF PREPARATION, AND USE THEREFORE

[76] Inventor: Huseyin Z. Ozel, Yildiz Posta Cad. 14/706, Gayrettepe, Istanbul, Turkey

[21] Appl. No.: 572,848

[22] Filed: Aug. 24, 1990

Related U.S. Application Data

[63] Continuation of Ser. No. 48,435, May 11, 1987, abandoned, which is a continuation-in-part of Ser. No. 862,720, May 13, 1986, abandoned.

[51] Int. Cl.$^5$ .............................................. A61K 35/78
[52] U.S. Cl. .................................................. 424/195.1
[58] Field of Search ..................................... 424/195.1

[56] References Cited

PUBLICATIONS

Ozel, Dirim, 4:172, 1972.
Ozel, Dirium, 12:565, 1974.
Taylor, et al., Texas Reports on Biol. and Med. 14:538, 1956.
Tarkowska, Acta Soci. Botanicorum Poloniae, 40:623, 1971.
Merck Index, 10th Ed, pp. 355, 979, 1413, 1983.
Woo, et al., Arch Pharm. Res. 2(2):127, 1979.
Chavan, et al, Bul of the Haffkin Inst., 11(3):68, 1983.
Mansuri, et al. Indian J. Phys. & All. Sci. 34(1):30, 1980.
Karawya, et al., Egyptian J. Pharm. Sci., 14(2):113, 1973.
Leporatti, et al., J. Ethno., 14:65, 1985.
Yamauchi, et al., Phytochem, 22(10):2211, 1983.
Tarkowska, Hereditas, 67:205, 1971.
Statz, et al., Cancer Treatment Reports, 60(8):999, 1976.
Hartwell, Cancer Treatment Reports 60(8):1031, 1976.
Duke, et al. in Med. Plants of China, Ref. Pub. pp. 97–98, 1985.

*Primary Examiner*—John W. Rollins
*Attorney, Agent, or Firm*—John R. Wetherell, Jr.

[57] ABSTRACT

The present invention is directed to extracts of the genus Nerium useful in ameliorating cell-prolferative disease, methods of preparing these extracts, and methods of using these extracts.

27 Claims, No Drawings

EXTRACTS OF NERIUM SPECIES, METHODS OF PREPARATION, AND USE THEREFORE

CROSS REFERENCE TO RELATED APPLICATION

This is a continuation of application Ser. No. 048,435 filed on May 11, 1987 now abandoned; which is a continuation-in-part of application Ser. No. 862,720, filed in the United States Patent and Trademark Office May 13, 1986, now abandoned.

BACKGROUND OF THE INVENTION

1. Field of the Invention

This invention is directed to extracts of plant species of the genus Neriuim which are useful in treating cell-proliferative diseases in animals. In addition, the invention is directed to methods of preparing these extracts and methods of using these extracts for the diagnosis and amelioration of cell-proliferative diseases in animals.

2. Description of the Background Art

Plants of the genus Nerium are members of the Apocynaceae family. These plants are native to Asia and the Mediterranean region and have been introduced as ornamental shrubs to most countries in Africa, South America and the southern United States. Within this genus, *Nerium oleander* is probably the best known.

This plant, also known as rose laurel, adelfa, and rosenlorbeer is toxic in its natural state and has caused deaths among humans, as well as household pets and farm animals. One leaf of oleander is considered potentially lethal to humans. Accidental poisoning in humans has occurred from chewing the flowers and from eating meat cooked over oleander branches or foods stirred with oleander stems. Smoke derived from the burning wood and leaves and honey manufactured from the nectar of oleander blossoms have been considered potentially dangerous in man.

Symptoms of poisoning, after a latent period of several hours, include severe abodminal pain, violent vomiting, cyanosis, tachycardia, hypotension, and hypothermia. In severe cases, in addition to these systems, an individual may exhibit drowsiness, mydriasis, vertigo, bloody diarrhea, cardiac irregularities, comma, respiratory paralysis, and death. In man, contact dermatitis has also been reported.

The presence of glycosides in a crude water extract from leaves of *N. oleander* has been studied for its effect on mitosis of meristematic root tip cells in *Allium cepa* (Tarkowska, *Acta Societatis Botanicorium Poloniae*:40: 624, 1971).

The known active components of the oleander are primarily oleandrin, neriine and other digitoxin-like glycosides. These glycosides are similar in physiologic action to digitalis and have apparently been used clinically in the treatment of human heart disease as a substitute for digitalis. However, in spite of the fact that the erleander can serve as a basis for these cardiac glycosides, it has never been scientifically demonstrated that extracts of this plant could be used to treat cell-proliferative diseases in animals.

SUMMARY OF THE INVENTION

It is object of the present invention to provide plant extracts of the genus Nerium that are useful in the treating of cell-proliferative diseases in animals.

It is another object of the present invention to produce these abstracts from the oleander (*Nerium oleander*).

Another object of the present invention is to provide methods for of preparing an extract useful in the treatment of cell-proliferative diseases in animals from plants of the genus Nerium, wherein these extracts are obtained by:

a. a dispersing plant matter of a Nerium species in a polar inorganic solvent;

b. heating the dispersed plant matter;

c. separating the heated solvent of step b from the plant matter; and d. heating the separated solvent of step c.

Still another object of the invention is to provide methods for the in vitro and in vivo diagnosis of cell-proliferative diseases in animals using extracts of plants who are members of the genus Nerium.

A further object of the invention is to provide methods for ameliorating cell-proliferative diseases in an animal using an extract of a plant of the genus Nerium.

The present invention thus relates to a new plant extract of the genus Nerium which is useful in the treatment of cell-proliferative diseases in animals. Unlike existing therapeutic modalities which usually have severe side-effects and rather narrow scope of diseases susceptibility, the ability of the extract of the invention to be effective in treating such a broad spectrum of cell-proliferative diseases, while at the same time demonstrating little in the way of side effects, is pioneering in terms of treating animals afflicted with these diseases.

DESCRIPTION OF THE PREFERRED EMBODIMENTS

The present invention relates to plant cell extracts of the genus Nerium which are useful for the treatment of cell-proliferative diseases. Preferred species of Nerium for preparation of extracts of the invention are *N. indicuim* and, especially, *N. oleander*.

The term "plant matter" denotes any part of the plant, although the less fibrous parts of the plant are generally more useful than fibrous parts such as, for example, roots or lower, woody parts of stems. The extracts of the invention are preferably prepared from the branches, leaves and flowers of the Nerium plant which can be sliced into pieces ranging in size from about 2 to about 2.5 cm in length. It is preferred to use plant matter harvested between about May and about September in preparing the extracts. Within about 1 week of collecting and slicing the plant material, the sliced plant material is suspended in a polar inorganic solvent, such as water, and heated to about 100° C. The heating process continues for about 2½ hours, during which time loss of liquid due to evaporation is compensated for by the addition of water to the vessel. At the end of the initial heat treatment, the density of the aqueous phase is determined. If the density is less than about 1010 the extract is again heated until the desired density is obtained. After the proper density is obtained, the mixture is allowed to cool to room temperature, filtered to remove large particulate matter, filtered again to eliminate small particulate matter and aliquoted into appropriate containers and sealed. After this second filtration, the sealed containers are again heated to about 100° C. for about 1 hour. This form of the extract is suitable for preparation of pomades (NOC), powders (NOP), gargles (NOG) and oral (NOO) medicaments. In preparing an extract suitable for use in injection form (NOI), the extract is again filtered, dispensed into sealed containers and again heated for about 1 hour at about 100° C.

The cell-proliferative disease ameliorating activity of the extracts of the invention are heat stable and can be extracted using polar inorganic solvents such as, for example, water and $CO_2$. However, any type or solvent can be used as long as it removes the cell-proliferative disease ameliorating activity from Nerium plant matter suspended in the solvent.

In addition, various other parameters of the extraction process such as, for example, time of heating, the manner in which the extract is heated and the size and number of filters which are utilized, can be modified. The time and temperature of heating can vary, the primary consideration being that heating is sufficiently long and high enough to sufficiently inactivate deleterious substances which may be present, while leaving the cell-proliferative disease ameliorating activity at a concentration useful for treating such disease. In this manner, higher temperatures may require shorter heating times and lower temperatures may require longer heating times. Regardless of the manner in which the process for producing the extracts of the invention might be modified the elimination of possible deleterious substances while maintaining therapeutically useful levels of cell-proliferative disease ameliorating activity can be monitored using the in vitro and in vivo tests described infra. Thus, those skilled in the art will be able to modify these parameters using routine experimentation.

The density of the extracts of the invention can vary from about 800 to about 1200, more preferably from about 900 to about 1100, most preferably from about 950 to about 1050. The final density of the extracts of the invention can vary as long as this variation is compensated for by appropriately adjusting the treatment dose of the extract. In all likelihood, higher density extracts would require a lower treatment dose whereas lower density extracts would require a higher treatment dose. The effect of variation in extract density is readily discerible by monitoring the activity of the extract as described infra in the in vitro and in vivo tests.

It is possible to determine if an extract of the genus Nerium has the activity of the extracts of the invention based upon known in vitro and in vivo tests. This can be based on the fact that the extracts of the invention when administered in vivo in normal mice show no apparent side effects when administered in single or repeated dosages subcutaneously at about 0.01, about 0.1 or about 1.0 ml/kg on such easily measurable parameters as body weight, weight of the spleen or thymus, blood leucocytes and the number and responsiveness of both resident or elicited peritoneal macrophages. Further, the extracts of the invention inhibit tumor growth in the syngeneic mouse tumor model.

When tested in vitro the extracts of the invention will inhibit murine monocyte activation and leucocyte proliferation. In humans, the extracts of the invention inhibit phorbol ester or zymosan induced chemiluminescence of monocytes, but not neutrophils.

Thus, it is readily discernable, based on these simple in vitro and in vivo characteristics, whether an extract of Nerium has the activity of the Nerium extracts of the invention.

The further purification and isolation of the activity present in the extract would be a matter of routine skill in the art. It is known that the cell-proliferative disease ameliorating activity is heat-stable and water extractable from plants of the genus Nerium. These physicochemical characteristics in combination with the known biological activities described supra, enable one of ordinary skill to readily isolate the cell-proliferative ameliorating activity present in extracts of the invention using routine separation techniques. The various fractions obtained using these separation techniques could, in turn, be monitored with respect to the known biological activity of the extract of the invention to, in effect, "trace" the activity throughout the various purification steps. For example, one could easily characterize the molecular weight range of the ameliorating activity by subjecting the extract of the invention to various well-known molecular weight sieving techniques such as, for example, gel filtration and/or selective filtration exclusion using membranes of different porosity such that only molecules of a certain size can penetrate through the membrane. Other common techniques which could be used are those which separate molecules based on ion-exchange principles such as, for example, DEAE- or CM-derived substrates. It would also be possible to isolate certain chemical fractions based on their specific binding activity such as, for example, using Detoxi-Gel TM (Pierce, Rockford, Ill.) to remove any undesirable endotoxin which might be present in the extract. As the biologically active fraction isolated from the extract of the invention becomes increasingly more purified, it is possible to utilize more sophisticated separation techniques such as high performance liquid chromatography (HPLC). Regardless of the routine separation and purification techniques which one of skill in the art would utilize to isolate a more purified form of the extract, the ability to monitor the biological activity disclosed supra, make the preparation of this fraction a matter of routine experimentation.

The characterization of the biological acticity suggest that the activity of the extracts of the invention potentiates an immunosuppressive effect on cells, possibly monocytes, in the immune system. It is reasonable that the extracts act, in effect, to suppress a suppressor effector cell subset which, in turn, allows the immune system to respond to the disease.

The term "cell-proliferative diseases" is meant to denote malignant as well as non-malignant cell populations which often appear morphologically to differ from the surrounding tissue. For example, the extract of the invention is useful in treating malignancies of the various organ systems, such as, for example, adenocarcinomas, lung, breast, lymphoid, gastrointestinal, and genito-urinary tract. Adenocarcimomas include malignancies such as most colon cancers, renal-cell carcinoma, prostate cancer, non-small carcinoma of the lung, cancer of the small intestine and cancer of the esophagus. The extract of the invention is also useful in treating non-malignant cell-proliferative diseases such as, for example, psorasis, pemphigus vulgaris, Behcet's syndrome, and lipid histiocytosis.

The term "treating" when used with respect to the extract of the invention is meant to denote both in vitro and in vivo diagnosis, as well as the in vivo amelioration of cell-proliferative diseases in animals. The term "animals" as used herein is meant to include both humans as well as non-humans.

Based upon the results of in vitro and in vivo testing using the extract of the invention, it is believed that the extract potentiates an immune response. The term "potentiates an immune response" means that the extract of the invention acts to enhance the ability of the overall immune response to ameliorate the cell-proliferative disease. When used in this manner, the term "ameliorate" denotes a lessening of the detrimental affect of the cell-proliferative disease on the host animal.

The term "diagnostically effective" means that the amount of NO extract administered is in quantity sufficient to elicit a rise in temperature of from about 38° C. to about 41° C. in those patients who are capable of responding favorably to therapy with NO extract.

The term "therapeutically effective" means that amount of NO extract which is capable of ameliorating the cell-proliferative disease.

In order to determine whether a patient is likely to benefit from therapy based upon the extract of the invention, a patient suspected of having a cell-proliferative disease is first screened using the injectable form (NOI) of the extract of the invention. This screening test is used with all patients suspected of having a malignant cell-proliferative disease and also with patients having more serious non-malignant cell-proliferative diseases such as, for example, lipid histiocytosis, Behcet's syndrome and pemphigus vulgaris. In preforming this test, the patient is injected subcutaneously with a small amount of NOI on 3 consecutive days. For example, a preferred test regimen is to inject a patient with about 0.3 ml, about 0.4 ml and about 0.5 ml of NOI on days 1, 2 and 3, respectively, of the test. However, with a patient who is negative in this range screening can be continued in about 0.1 ml increments to a total of about 1.0 ml on consecutive days to determine whether a patient is likely to respond to NO extract therapy. If the patient responds to the injection on any of these days by developing a fever, preferably ranging from about 38° C. to about 41° C., then the patient is a candidate for therapy with the extract of the invention (NO extract). It is preferable to utilize a dose of NO extract which will cause a fever in the range of from about 38° C. to about 39° C. in order to minimize patient discomfort. Usually, the fever occurs within about 4 hours following intramuscular injection and continues for a period of from about 2 to about 4 hours. Often, patients will experience chills prior to the occurrance of the fever.

Once a patient is selected for therapy with an NO extract of the invention, an initial therapeutic regimen is selected which may comprise NO extract in various forms. Thus, depending on the condition of the patient and the nature of the cell-proliferative disease, a given patient might be placed on either injectable NO extract (NOI), oral NO extract (NOO), a pomade of NO extract (NOC), a powder containing NO extract (NOP), a gargle of NO extract (NOG) or any combination of these compositions containing NO extract. Usually patients with malignant cell-proliferative diseases and those with a more serious non-malignant diseases will receive NOI. Patients with less serious diseases such as, for example, the milder forms of psoraisis and the like, can be treated with an NOC composition.

The dosage for administration of NOI is usually about 0.05 to about 2.0 ml, more preferably about 0.10 to about 1.0 ml, most preferably about 0.3 ml to about 0.7 ml usually administered once a day or every other day.

Patients receiving NOO usually receive about 0.1 ml to about 2.0 ml, more preferably about 0.2 ml to about 1.0 ml, most preferably about 0.3 ml to about 0.7 ml, 3 times per day after meals.

The initial therapeutic regimen is continued at least until the patient no longer develops a fever following administration of NOI. This time may range from about two weeks to about one year depending on the response of the patient. At the end of this time, patients should be examined to determine whether any grossly detectable signs of disease remain. If the patient still shows signs of disease, the initial therapeutic regimen is continued until the disease is no longer detectable by standard techniques such as, for example, tomography or X-ray. However, if the patient at this time does not have any grossly detectable signs of disease, the patient is then placed on maintenance NO therapy. This maintenance therapy will typically be at about the same dose level as that utilized during the initial therapeutic regimen, however, the administration will be much less frequent, for example, every 2 weeks. The maintenance therapy may continue from about 3 months to about 3 years depending upon such factors as the severity of the cell-proliferative disease of the patient when first examined and how long it was necessary to maintain the patient on the initial therapeutic regimen.

It has been observed that the maximum therapeutic dose developed in testing thus far for NOI is about 1 ml/day and for NOO about 2.5 ml/day, based on a 60 kg patient. However, in all liklihood much higher does of NO extract can be utilized and thereby shorten the time necessary to achieve optimal amelioration of the cell-proliferative disease. In using these higher doses of NO extract it may be advantageous to also administer, for example, an antipyretic drug in order to lessen the effects of any high fever which might accompany such dosages.

When therapeutic doses of NO was administered to patients with malignant diseases the following associated effects may occur:

a. when administered for the first time, NOO sometimes caused nausea, vomiting and diarrhea. However, these symptoms disappeared in a few days following application of symptomatic therapy.

b. increased micturition; in some cases itching and exfoliation occurred. These effects could usually be eliminated by treatment with antihistamine or cortisone. If treatment with these agents was unsuccessful the thereapy was abandoned.

c. occasionally local pain occurred at the site of an NIO injection which was treated with a local anesthetic.

d. some patients develop, for a short time, pain in the tumors following an NOI injection. In the case of sharp pain, an anesthetic can be administered. The occurence of the pain helped reveal the location of the tumors.

e. most patients experienced pain in their breast glands similar to that experienced during adolescene. This pain was somtimes associated with an increase in libidinous propensity.

f. during the initial therapeutic regimen all patients demonstrated a rise in total leucocyte count up to from about 12,000 to about 24,000.

g. some patients with anemic symptoms developed tachycardia and cardiotonic medicines were applied. However, during NOI therapy no patients experienced nervous system or vision complications.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcoholic-/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidents, chelating agents and inert gases and the like.

Liquid dosage forms for oral administration will generally comprise NOO alone or in a composition additionally containing insipients such as emulsions, suspension, solutions, syrups and elixirs containing inert diluents commonly used in the art, such as purified water, sugars, polysacroids, silicate gels, gelatin, or an alcohol. In addition to the inert diluents, these compositions can also include factors such as wetting agents, emulsifying and suspending agents, and sweetening, flavoring, and perfuming agents.

The invention also relates to a method for preparing a medicament or pharmaceutical composition comprising the Nerium extract of the invention, the medicament being used for therapy of cell-proliferative diseases.

The above disclosure generally describes the present invention. A more complete understanding can be obtained by reference to the following specific examples which are provided herein for purposes of illustration only and are not intended to limit the scope of the invention.

EXAMPLE 1

Preparation of Nerium Oleander Extract

The branches, leaves and flowers of *Nerium oleander* were collected and sliced into pieces from about 2 to about 2.5 cm in length. Within about one week following collection and slicing of the plant material an extract was prepared from the plant material by adding approximately 2 kg of sliced plant material to about 10 kg of distilled water in an enamel container. This mixture of material was heated until it started boiling after which time the plant material was boiled for about 2.5 hours. During boiling, distilled water was added to the container to compensate for evaporation in order to maintain a constant water level in the container. At the end of about 2.5 hours of boiling the density of the aqueous phase extract should be about 1010 using a buoyancy densitometer. If the density is less than about 1010, the extract should be boiled for about another half hour until the desired density is attained through further evaporation. After boiling, the mixture is allowed to stand at room temperature for a period of about 6 to about 8 hours. Next, the mixture is processed through a coarse filter in order to remove large particulate matter should such leaves and branches. The filtrate was then subjected to a second filtration through a medical filter and decanted into 700 ml bottles with tight lids. Within about 4 hours after this last filtration step the bottles were heated to about 100° C. for about 1 hour. If this second treatment does not occur within about 4 hours, the dark brown color of the extract changes to a bright yellow color and the extract should not be used. Following this second heat treatment the bottles are stored at room temperature for about 10 hours. In this form, the extract has a shelf life of about one year when stored at about 2° to about 4° C. This form of the extract is used to prepare pomades, powders, gargles and oral medicaments.

In order to prepare an extract for use in injection (NOI), the oral form of the extract described supra was subjected to filtration with a medical filter paper with porosity of from about 2.9 microns to about 4.8 microns and dispensed into 10 ml bottles with rubber lids and sealed aluminum covers. The sealed bottles were then sterilized at about 100° C. for about 1 hour. This form of the extract is stable for about three months when stored at about 2° to about 4° C.

A pomade (pomade A) containing the extract of the invention was prepared using about 19% by weight NOO, about 2.5% by weight flower pollen, about 59.5% by weight Vaseline, about 7.1% by weight lanoline and about 11.9% by weight almond oil. This pomade is useful in the treatment of dermic cancers.

Another pomade of NO (pomade B) is prepared using the same ingredients and method as described for pomade A except in addition about 5% by weight salicylic acid is added to the composition.

A powder containing NO can be prepared by combining 2 ml Bepanthene (ROCHE-Turkey), 500 units of Alfasilin (FACO-Turkey), 1 ml ANTISTINE (CIBA-Turkey), 0.5 ml ethyl alcohol (70 proof pure) and 0.5 ml NOO.

A mouthwash useful for gargling comprises a mixture of water and about 5% by weight NOO.

EXAMPLE 2

Administration of the Extract of the Invention

Patients suspected of having a malignant cell-proliferative disease are initially screened to determine whether they will respond effectively to administration of the extract of the invention. In this initial screening test the patient is injected intramuscularly with about 0.3 ml, about 0.4 ml and about 0.5 ml of NOI on the first, second, and third days, respectively, of the test.

A positive response, which indicates that the patient will respond to the extract of the invention, is indicated by a rise in the temperature of the patient to about 38° C. to about 41° C. depending on the dose of extract administered. This fever takes place within about 4 hours following the intramuscular injection and continues for a period of from about 2 to about 4 hours. It has been noticed that patients often feel cold before they experience a rise in body temperature. As a general rule, the greater the rise in temperature of the patient, the shorter the length of therapy. The optimum range for fever has been found to be from about 38° C. to about 39° C. in order to minimize discomfort to the patient. Experimental data obtained thus far indicate that approximately 70% of those patients that present with malignant cell-proliferative diseases show a positive reaction to the screening test. The positive response, in turn, indicates that therapy with the NO extract will ameliorate the disease.

Those patients which are positive for the screening test as described supra are placed on an initial therapeutic regimen utilizing various forms of the extract of the invention. Typically, a patient is administered from about 0.3 to about 0.7 ml of NOI intramuscularly per day depending upon the rise in temperature of the patient. In cases of gastrointestinal malignancies, injections of NOI are often used in combination with oral administration of the extract (NOO). Additionally, in those patients have dermic cancers, a pomade of the extract (usually pomade A) was applied in combination with injections of NOI. The initial therapeutic regimen was performed at least until injection with NOI no longer caused a rise in the patient's body temperature. It has been found that the patient will generally receive this initial therapeutic regimen for a period from about 20 days to about one year and that this period of time depends upon the severity of the malignancy. In most cases patients can resume a normal lifestyle following completion of the initial therapeutic regimen.

Following completion of a normal therapeutic regimen a patient normally was then placed on a maintenance therapeutic regimen for a period of time ranging from about six months to about three years. Typically, during this period of time the patient receives about 0.4 ml of NOI administered about every two weeks. Usually a patient will be on maintenance therapy for a time roughly equivalent to the amount of time required for the initial therapeutic regimen. In those instances where a patient develops a fever during maintenance therapy following administration of NOI the patient is returned to an initial therapeutic regimen.

In the approximately 30% of cases where patients did not show a positive response to the screening test, even at test doses of up to about 0.8 ml NOI, no regression of malignancy nor rise in fever was seen. However, patients who elected to be administered NOI have been found to experience less pain and do not need to use any analgesic supportive drug therapy.

In patients presenting with non-malignant cell-proliferative diseases such as, for example, psoraisis, the screening test does not have to be formed and these patients do not usually experience a rise in fever. Typically, patients with psoraisis are placed on a regimen consisting of 0.3 ml of NOI administered intramuscularly every two days, 0.5 ml of NOO administered three times per day and NO pomade B applied once a day. This therapeutic regimen continues until all symptoms disappear, usually in about 20 days to about four months after initiation of therapy. No maintenance therapy is usually needed.

Those patients who present with more serious non-malignant cell-proliferative diseases such as, for example, lipid histiocytosis (Niemann-Pick disease), Behcet's syndrome and pemphigus vulgaris, are usually screened using NOI and, if positive, treated with an initial therapeutic regimen basically the same as that administered in the treatment of malignant cell-proliferative diseases. Often it is not necessary that such patients be placed on maintenance therapy.

EXAMPLE 3

Clinical Efficacy of no Extract in the Amelioration of Malignant Cell-Proliferative Disorders Between January 1981 and December, 1985, 494 patients with inoperable, advanced malignant diseases were tested with NOI. All malignancy had previously been diagnosed at various specialized medical institutions in Turkey and abroad. The malignancies of these patients had progressed to a state where they could no longer benefit from existing anti-tumor therapies. These 494 cases included examples of almost all varieties of malignancies and were found in various organs. The results of this clinical testing are summarized in Table I.

TABLE I

RESPONSE OF PATIENTS WITH VARIOUS MALIGNANCIES TO NOI

| PRIMARY TUMOR | RESPONSE | PRIOR TREATMENT | | | | TOTAL |
|---|---|---|---|---|---|---|
| | | NONE | CHEMO-THERAPY | RADIATION | CHEMOTHERAPY AND RADIATION | |
| LUNG | + | 55(65)[a] | 0 | 11(61) | 2(29) | 68(61) |
| | − | 30(35) | 1 | 7(39) | 5(71) | 43(39) |
| GASTRO-INTESTINAL | + | 68(63) | 4 | 1 | 0 | 73(63) |
| | − | 40(37) | 0 | 1 | 1 | 42(37) |
| LARYNX | + | 33(92) | 0 | 7(70) | 3(60) | 43(84) |
| | − | 3(8) | 0 | 3(30) | 2(40) | 8(16) |
| OESO-PHAGUS | + | 10(77) | 0 | 0 | 0 | 10(77) |
| | − | 3(23) | 0 | 0 | 0 | 3(23) |
| UROGENITAL | + | 24(83) | 0 | 10 | 5(63) | 39(81) |
| | − | 5(17) | 1 | 0 | 3(37) | 9(19) |
| BRAIN, NERVOUS SYSTEM | + | 3(60) | 0 | 1 | 0 | 4(29) |
| | − | 2(40) | 0 | 1 | 2 | 5(71) |
| BONE | + | 6(86) | 0 | 1 | 0 | 7(64) |
| | − | 1(14) | 0 | 2 | 1 | 4(36) |
| LYMPHATIC SYSTEM | + | 17(77) | 2 | 2 | 0 | 21(64) |
| | − | 5(23) | 1 | 2 | 4 | 12(26) |
| BREAST | + | 28(67) | 2 | 6(86) | 4(40) | 40(64) |
| | − | 14(33) | 1 | 1(14) | 6(60) | 22(36) |
| EPIDERMIC | + | 9(90) | 0 | 0 | 0 | 9(75) |
| | − | 1(10) | 0 | 0 | 2 | 3(25) |
| LEUKEMIA | + | 5(45) | 4(50) | 0 | 0 | 9(47) |
| | − | 6(55) | 4(50) | 0 | 0 | 10(53) |
| SARCOMA | + | 4(80) | 0 | 0 | 1 | 5(63) |
| | − | 1(20) | 1 | 0 | 1 | 3(37) |
| THYROID | + | 1 | 1 | 0 | 0 | 2 |
| | − | 0 | 0 | 0 | 0 | 0 |
| OVERALL REACTIVITY TOTALS | + | 263(70) | 13(59) | 39(70) | 15(36) | 330(67) |
| | − | 111(30) | 9(41) | 17(30) | 27(64) | 164(33) |

[a]( ) = percent

Table 1 shows the positive reaction rates of NOI on patients with various malignant diseases. The malignancies are grouped based on primary tumor location. Patients presenting with primary tumors of gastrointestinal origin encompasses origination of primary tumors in such areas as the stomach, intestine, colon, rectum, pancreas, liver or gall bladder. Those patients in the larynx category include those whose primary tumors originated from the larynx, tongue, pharynx, tonsil or nose. Patients grouped in the urogenital category include those whose primary tumors originated in the kidney, suprarenal gland, vesica, prostate, ovary, uterus or urethra. Melanoma is included among those patients classified as having epidermic primary tumors. Patients with inoperable and advanced malignant diseases who had received no chemotherapy or radiation showed a 70% positive response to NOI therapy. Of those patients presenting with prior treatment, 59% of the patients who had previously received chemotherapy responded to NOI, 70% of those patients which had previously received radiation responded to NOI and 36% of those patients who had previously received both chemotherapy and radiation responded to NOI. These figures indicate that while pretreatment with chemotherapy or radiation does not have a significant effect on a patient's response to NOI therapy, patients who are pretreated in this manner have a significantly reduced likelihood of responding to NOI therapy compared to patients who were not pretreated or had been pretreated with only chemotherapy or only radiation.

TABLE II

| PRIMARY TUMOR | RESPONSE | MALE | FEMALE | TOTAL |
|---|---|---|---|---|
| DISTRIBUTION BY SEX OF PATIENTS SCREENED FOR NOI THERAPY | | | | |
| LUNG | + | 61 | 7 | 68 |
|  | − | 37 | 6 | 43 |
| GASTRO-INTESTINAL | + | 36 | 37 | 73 |
|  | − | 32 | 10 | 42 |
| LARYNX | + | 37 | 6 | 43 |
|  | − | 6 | 2 | 8 |
| OESOPHAGUS | + | 7 | 3 | 10 |
|  | − | 2 | 1 | 3 |
| UROGENITAL | + | 16 | 23 | 39 |
|  | − | 2 | 7 | 9 |
| BRAIN, NERVOUS SYSTEM | + | 3 | 1 | 4 |
|  | − | 4 | 1 | 5 |
| BONE | + | 5 | 2 | 7 |
|  | − | 3 | 1 | 4 |
| LYMPHATIC SYSTEM | + | 19 | 2 | 21 |
|  | − | 7 | 5 | 12 |
| BREAST | + | 2 | 38 | 40 |
|  | − | 0 | 22 | 22 |
| EPIDERMIC | + | 5 | 4 | 9 |
|  | − | 3 | 0 | 3 |
| LEUKEMIA | + | 7 | 2 | 9 |
|  | − | 8 | 2 | 10 |
| SARCOMA | + | 2 | 3 | 5 |
|  | − | 1 | 2 | 3 |
| THYROID | + | 1 | 1 | 2 |
|  | − | 0 | 0 | 0 |
| OVERALL RESPONSE | + | 201 | 129 | 330 |
|  | − | 105 | 59 | 164 |

Table II shows the distribution of these 494 patients with respect to primary malignant tumor site, sex and responsiveness to NOI. Of these patients, 62% (306) were male. Of the patients in this study, the response to NOI was 66% for males (201/306) and 68% for females (129/188). Thus, the sex of the patient had no apparent affect on the likelihood of a positive reaction to NOI.

EXAMPLE NO. 4

Case Report: Lipid Histiocytosis

The patient, 22 years of age, was diagnosed as having lipid histiocytosis on May 10, 1976 at the Royal National Orthopedic Hospital in London. After returning to Turkey the patient developed pain more frequently and in more locations. When he was examined on Jun. 15, 1976 he had lost 6 kg in weight, had started using analgesics and was in very poor medical condition. The pain, which occurred on both tibia, shoulders and humerus, was so sharp that it was very difficult to examine the patient. The patient gave a positive reaction to the NOI screen. Following this, the patient was started on an initial regimen of 0.3 ml NOI every 24 hours and developed a fever of 39° C. After 20 days of this therapy, there was a lessening of pain. After an additional 1½ months of initial therapy the patient was free of pain and had regained the weight which had been lost. The patient remained on the initial therapeutic regimen for 6 months after which time he was placed on maintenance therapy for one year. During this time he was administered 0.4 ml of NOI every two weeks. After completion of the initial therapeutic regimen the patient was able to return to work and as of Apr. 1, 1986, was found to be in complete health.

EXAMPLE 5

Case Report: Inoperable Antrum Cancer

The patient started to develop gastric pain in 1969 when he was 39 years of age. Following x-ray examinations he was initially diagnosed as having a duodenum ulcer and was treated accordingly. In March, 1974 he developed more pain and presented to the Capa Medical Faculty of Istanbul University. After examination of his previous radiographs and his present symptoms a surgical operation was performed on Mar. 8, 1974 at the External Diseases Clinic of the Capa Medical Faculty. Laparatomy revealed a tumor mass in the antrum, bloody acid in the abdomen, multiple hipatic metastases. On these bases the patient was diagnosed as having inoperable antrum cancer. The patient was discharged from the clinic 10 days later. On Apr. 12, 1974 he presented to the Haydarpasa Numune Hospital in Instanbul with an abundant gastric hemorrage. Although coagulative treatment and continuous blood transfusions were applied, no success was achieved in stopping the hemorrage. After studying the previous examination report from the Capa Medical Faculty, the experts at Haydarpasa Numune Hospital stopped treating the patient and stated that nothing could be done. The inventor examined the patient for the first time at Haydarpasa Numune Hospital and found acid present in the abdomen, arterial tension of 6/4 and a filiforme pulse. When the patient was screened with NOI on Apr. 15, 1974 a positive reaction was observed and he was placed on an initial therapeutic regimen of 0.3 ml NOI daily in combination with 0.5 ml of oral NOO administered 3 times per day after meals. On Apr. 18, 1974 he was dismissed from the hospital in order to spend the remainder of his life at home. X-ray examination done on Jun. 20, 1974 showed the existence of "antrum Ca."On Aug. 27, 1974 the patient returned to the Haydarpasa Numune Hospital for an examination and was diagnosed as having "gastric antrum, minor curvature sclereux annular Ca." and was given another four months leave from his job with the government. The initial therapy, comprising a single course of 0.3 ml of NOI which caused a fever of 39° C., ended on Sept. 3, 1974 when the patient failed to show a fever following injection. At this time, the patient was placed on maintenance therapy which consisted of 0.4 ml NOI every two days until Jan. 1, 1975 at which time the regimen was modified to an injection of 0.4 ml NOI once a week for an additional six months. In addition to the NOI injections, the patient was also given oral doses of NOO (0.5 ml three times per day after meals) from the time of initial screening until April, 1976.

The patient was in complete regression at the end of the initial therapy. On Apr. 2, 1975 he presented to the Haydarpasa Numune Hospital for examination. On Apr. 18, 1975 the Health Council of the Hospital reported that there was probably a mistake in the previous reports of the Capa Medical Faculty and their own, that the patient was in complete health and was readmitted to work.

EXAMPLE 6

CASE REPORT: HODGKIN'S GRANULOMA

At age 46, the patient presented to Izmir State Hospital on May 5, 1973 with weakness and swollen neck lymph nodes. Inspection revealed two lymphadenopathies on the neck. Initially, the patient was diagnosed as having adenite tuberculosis and the use of antituberculosis medicines was recommended.

In June, 1973 the patient returned to the same hospital with the same symptoms. One of the neck lymph nodes was excised and upon histologic examination revealed Hodgkin's granuloma. The report of the Hospital Health Council issued on Jun. 15, 1973.

On Jun. 18, 1973 the patient was examined by the inventor. The patient had a scar on his neck, weakness and weight loss related symptoms. He had palpable thickening in both inguinal and arm pit lymph nodes as well as his neck lymph nodes. In screening with NOI (0.3 ml) the patient responded with a fever of 40° C. He was placed on an initial therapeutic regimen wherein he was administered 0.3 ml NOI daily. After one month the patient no longer demonstrated a fever following injection. During the one month of initial therapy, changes in lymphocytes, as a percent of total leucocytes, were recorded as follows: 46% on Jun. 18, 1973; 16% on Jun. 26, 1973; and 26% on Jul. 4, 1973. Only one inguinal lymph node palpated weakly when he was examined on Jul. 25, 1973. This lymph node was excised and sent to Istanbul University Cancer Institute for histologic examination and diagnosed as "unorderly follicule hyperelasie" with no sign of malignancy. The patient was placed on maintenance therapy at an initial dose of 0.3 ml NOI at weekly intervals. He was also given oral NOO starting from Feb. 1, 1974 (0.5 ml, 3 times per day) for 1 year. Following the initial therapeutic regimen the patient returned to work and since this time has been in complete regression.

EXAMPLE 7

CASE REPORT: JUXTACORTICAL OSTEOGENIC SARCOMA

The patient presented to Karaman State Hospital in March, 1973 when he was 17 years of age with pain and swelling occurring in the right leg. A tumor was located which abutted from the lower right posterior distal femur and was locally excised. Histologic examination of the tumor was done at the Istanbul University Cancer Institute and diagnosed as "juxtacortical osteogonic sarcoma (paraosteal sarcoma)."

Later, the patient experienced a local relapse and came to the inventor on Oct. 1, 1973. A hard tumoral mass (20×10×5 cm) was detected under the scar and two inguinal right lymph nodes (1×1×1 cm and 2×2×2 cm) were palpated. Roentgenograms taken on Oct. 6, 1973 showed the presence of osteosarcoma with uptake in the region of the distal femur.

Since the patient was reluctant for amputation, and swollen lymph nodes were present, the patient was screened for NOI therapy and gave a positive response. The patient was placed on an initial therapeutic regimen of 0.3 ml NOI every 24 hours which caused a fever of 39° C. By day 15 following initiation of therapy, the lymph nodes had disappeared, the tumor in the leg had decreased in size, separated from the femur and become mobile. The tumor was then easily excised on Oct. 24, 1973 and entire resected specimen (the tumor and surrounding soft tissue) sent to Instanbul University Cancer Institute for histologic examination. The Cancer Institute diagnosed the specimen as "chondro fibro myxoma" with no sign of malignancy. A roentgenogram taken on Nov. 4, 1973 showed no sign of sarcoma, but the lower distal femur had eroded due to the previous sarcoma.

A year later, the femur broke in the region eroded by the tumor and although the leg was immobilized for a long period of time no recovery of the fracture was achieved. It was finally necessary to amputate the leg at the proximal femur. Since this time the patient has used a leg prothesis and is in complete regression.

EXAMPLE 8

Case Report: Inoperable Cervix Cancer

At age 59, the patient was diagnosed in November, 1975 at the Medical Faculty of Ankara University as having inoperable cervix flat cell carcinoma. A diagnosis report dated Nov. 10, 1975 also stated that the patient had received radiotherapy.

In January, 1976 blood was detected in the feces. On Feb. 20, 1976 patient was transferred from the Radiotherapy Clinic of Ankara University to the Clinic of Gastroenterology of that University. A diverting colostomy was later performed in the General Surgery Department of the Cukurova University Medical Faculty. Disseminated malignancy was observed in the pelvic and rectum. The report on the patient, issued by the same clinic, diagnosed the malignancy as an "inoperable cervix ca.-colostomy" and the patient placed on a regimen of morphine.

When the pain became sharper, a second report of the Cukurova University Medical Faculty on Mar. 8, 1977 stated that "the patient was to be injected with 7 ampules of morphine per day."

On Mar. 10, 1977 the patient was examined by the inventor. She was in extremely poor medical condition and was receiving injections of morphine every 3 hours. She has a diverting colostomy on the lower left quadrant of the abdomen. The anus was totally blocked with tumors. Other bloody tumors as big as almonds and similar in shape to cauliflower has developed around the anus. The upper region of the pubis was hardened due to previous radiotherapy. A test screen with NOI was positive and the patient was placed on an initial therapeutic regimen of 0.3 ml NOI every 24 hours. At this dose the patient experience an increase in temperature to 38.5° C. Since the patient was in extreme pain, she was taught how to apply the NO therapy and was allowed to return to her home where she carried on the treatment. Six months later, on Sep. 10, 1977 she presented to the inventor for an examination. She had stopped using morphine and the lesions had partially regressed, but she was still experiencing a rise in body temperature to 38°-39° C. following injection of NOI. It was recommended that she maintain the treatment and was sent home. On Feb. 8, 1978 she was re-examined by the inventor. At this time all lesions had completely regressed. Inspection of the rectal area revealed no sign of any tumor. The patient refused to have another surgical operation to re-divert the colostomy to normal and returned home. For this patient the initial therapeutic regimen was continued for 11 months before the initiation of maintenance therapy. During the 3 years that the patient was on maintenance therapy she was administered 0.4 ml of NOI every two weeks. In addition to the injections of NOI during the initial therapeutic regimen and during the maintenance therapy, the patient received oral NOO at a dose of 3×0.5 ml per day after meals. The patient has continued to be examined twice a year by the inventor and as of Apr. 14, 1986 was still in complete regression.

EXAMPLE 9

Case Report: Class V Undifferentiated Carcinoma

In late 1976 the patient developed frontal chest pain and dyspnea which were unaffected by analgesics. On Feb. 29, 1977 she presented at age 72 to the Ankara Military Air Force Hospital where a biospsy was performed and histologic diagnosis revealed the presence of bronchial cancer. On Apr. 21, 1977 the patient presented to the Izmir Chest Diseases Hospital and on Apr. 26, 1977 to the Etimesut Oncology Hospital. Both of these hospitals corroborated the diagnosis of the Air Force Hospital. The patient refused radiotherapy recommended by the Oncology Hospital and presented on May 6, 1977 to the Ankara University Chest Diseases Clinic.

Roentgenograms and tomography taken on May 6, 1977 and bronchoscopy performed on May 13, 1977 revealed a lesion in the upper right apical segment. A biopsy was performed with a transcranial needle and histological examination revealed "Class V Undifferentiated Ca." It was recommended that the patient be placed on symptomatic medicines and she was dismissed from the hospital.

On Sep. 10, 1977 the patient was examined by the inventor. Palpation of the chest veins showed an increase in volume, there was edema in the face and neck and symptoms of dyspnea and chest pain. When the patient was screened with 0.3 ml NOI she experienced a fever of 40° C. She was placed on an initial therapeutic regimen of 0.2 ml NOI every 24 hours. Within 6 months all symptoms had disappeared and at the end of 12 months there was no indication of fever following injection of NOI. The patient was then placed on maintenance therapy of 0.2 ml NOI every two weeks for one year.

In September, 1979 the patient experienced a heart attack, but recovered. She has been in complete regression and a roentgenogram taken on Mar. 27, 1986 was negative.

EXAMPLE 10

CASE REPORT: EPIDERMOID CANCER

The patient at age 56 presented to various hospitals in September, 1983 complaining of pain in both shoulders. X-ray examination revealed two lesions 5 cm in diameter in both upper lobes of the lungs. As a first diagnosis, tuberculosis or cyst echinococose were suggested and the patient was admitted on Oct. 4, 1983 to the Sureyyapasa Chest Diseases Hospital for a one month examination period. During this time roentgenograms were taken and Casoni and Weinberg tests were found to be negative. Tomographic examination revealed two lesions 5 cm in diameter in both upper lobes of the lungs. Bronchoscopic examination, biopsy and histologic examinations revealed "epidermoid Ca." The report stating this diagnosis was issued by the Health Council of the Hospital on Nov. 1, 1983 and recommended that the patient be dismissed since nothing could be done.

On Dec. 1, 1983 the patient was examined by the inventor. He had pain in his posterior chest and shoulders and was using analgesics to lessen the pain. When screened with NOI his reaction was positive and the patient was placed on a initial therapeutic regimen of 0.3 ml NOI daily. Following injection of NOI the patient experienced a fever of 39° C. The initial therapeutic regimen was continued until September, 1984 at which time the patient was placed on maintenance therapy of 0.4 ml NOI administered every two weeks for an additional 6 months. Following completion of the initial therapeutic regimen the patient has led a normal life. A roentgenogram taken on Apr. 4, 1986 was negative.

EXAMPLE 11

CASE REPORT: HEAD OF PANCREAS CANCER WITH HEPATIC METASTASES

At age 48, the patient presented to a local physician on Sep. 20, 1984 with weakness, loss of weight, abdominal pain and icterus symptoms. Ultrasonic examination revealed "head of pancreas Ca."

On Sep. 21, 1984 a second ultrasonic examination was done at the Selanik Gastroenterology Laboratory and resulted in a diagnosis of "head of Pancreas Ca 2×1.5 cm dia. hepatic metastases in the near apex right lobe." On Sep. 29, 1984 the patient underwent laparatomy at Kayseri Hayat Hospital. The laparatomy report stated "the patient presented to the hospital with head of pancreas Ca. diagnosis . . . a hard tumoral mass occupying the head and half of the pancreas body was detected . . . big olive sized hard, probably metastatic mass was detected in the middle of the left hepatic lobe. Cholecystojejunostomie-Braun anastomose was then performed in order to treat blockage icterus of the patient."

On Oct. 15, 1984 the patient was examined by the inventor. At this time the intensity of icterus was reduced and the patient was in poor medical condition. A test screen utilizing 0.3 ml of NOI resulted in a fever of 38° C. Following the test screen the patient was placed on an initial therapeutic regimen of 0.4 ml NOI daily and 0.5 ml NOO given 3 times per day after meals. By Apr. 22, 1985 the symptoms had disappeared and no fever was observed. On this same date, ultrasonic examination still revealed "head of pancreas Ca., dilated calices in the left kidney and hepatic metastases." Following this report the initial therapeutic regimen was extended for another 3 months at the same dose levels. During this 3 month period no rise in fever was observed. The patient was not placed on maintenance therapy.

On Apr. 5, 1986 the patient was again examined by the inventor and showed no apparent clinical symptoms. On Apr. 3, 1986 ultrasonic examination stated as diagnosis "calculus in right hepatic lobe, mass at the head of pancreas, dilation in pancreas canal." The report defined the mass that was present as "hypoechogene." The unusual change of previously malignant tumors to nonmalignant masses has been encountered in numerous other cases of patients treated with NOI. Such as, for example, Examples 6 and 7.

Since Apr. 22, 1985 the patient has lived a normal life and as of Apr. 5, 1986 appeared normal.

EXAMPLE 12

Case Report: Psoriasis

The patient first noticed inflammation on the skin of both knees in 1958. She attended various doctors and hospitals and was diagnosed as having psoriasis. After trying various therapies with no success, she stopped visiting hospitals when she was told that there was no effective cure for psoriasis.

On Apr. 4, 1986, the patient was examined, at age 50, by the inventor. During examination, psoriatic lesions were noted on both knees. The patient was placed on an initial therapeutic regimen of 0.3 ml NOI administered at 2-day intervals and 0.5 ml NOO administered 3 times a day after meals. In addition, the patient applied topically NO pomade B daily. After receiving the first 3 NOI injections by the inventor, the patient was given a stock of NOI, NOO and NO pomade B for treatment in her home.

On Nov. 28, 1986, the patient was examined at her home and stated that she had administered 5 additional NOI injections and that she had used the NOO and NO pomade B as precribed for 20 days until the medicaments were used up. Because her lesions had completely healed, she had not felt necessary to re-contact the inventor. At the time of her examination on Nov. 28, 1986, while scars from her previous psoriatic lesions were present, there was no evidence of psoriasis.

EXAMPLE 13

Use of NOI for Cancer Diagnosis

A. Twenty-two patients suspected of having malignancies were tested using the NOI screen. Positive reactions were seen in 17 of these patients, while 5 gave no reaction. Biopsies were then performed on all 22 patients and the resected specimens were examined histologically. The histological examinations confirmed that the 17 patients that gave positive reactions to the NOI screen had cancer. Of the 5 patients that did not respond to the NOI diagnostic screen, 4 showed no evidence of malignancy whereas 1 of these 5 patients was diagnosed as having cancer despite the negative reaction in the NOI diagnostic screen.

B. Ten healthy individuals were given 0.3 ml NOI in a diagnostic test screen. One patient showed a positive reaction, whereas the remaining 9 showed no reaction. The one patient responding to NOI had a beauty mark in the facial area. It is known that these marks may develop into a malignancy in the latter stages of life. When the beauty mark was excised and examined histologically, it was diagnosed as being cancerous. After excision of the beauty mark, the patient continued to show a postive reaction to NOI and so underwent NO therapy until the patient no longer developed a fever following administration of NOI.

The invention now being fully described, it will be apparent to one of ordinary skill in the art that many changes and modifications can be made without departing from the spirit or scope of the invention.

I claim:

1. A polysaccharide enriched extract of Nerium species containing an immunologically active polysaccharide useful in treating cell-proliferative disease in mammals, wherein the active polysaccharide comprises acidic homopolygalacturonans or arabinogalaturonans.

2. The extract of claim 1, wherein said Nerium species is *Nerium oleander*.

3. An extract of Nerium species containing an immunologically active polysaccharide useful in ameliorating cell-proliferative disease in mammals obtained by:
   a. dispersing plant matter of said Nerium species in a polar inorganic solvent;
   b. heating said dispersed plant matter;
   c. separating the heated solvent of step b from said plant matter; and
   d. heating the separated solvent of step c.

4. The extract of claim 3, further comprising:
   e. filtering the heated solvent step d; and
   f. heating the filtered solvent of step e.

5. The extract of claim 3, wherein said solvent is water.

6. The extract of claim 3, wherein said heating is carried out for a time sufficient to obtain a density of said solvent of about 1010.

7. The extract of claim 3, wherein said Nerium species in *Nerium oleander*.

8. An extract of *Nerium oleander* containing an immunologically active polysaccharide useful in ameliorating cell-proliferative disease in mammals obtained by:
   a. dispersing plant matter of said *Nerium oleander* in water;
   b. heating said dispersed plant matter for about 2.5 hours at about 100° C.;
   c. separating the heated water from said plant matter; and
   d. heating the separated water of step c for about 2.5 hours at about 100° C. to obtain a density of about 1010.

9. The extract of claim 8, further comprising:
   e. filtering the heated water of step d; and
   f. heating said filtered water of step e for about 1 hour at about 100° C.

10. The extract of claim 8, wherein said plant matter is chopped leaves, stems and flowers.

11. A method of ameliorating cell-proliferative disease in a mammal which comprises:
    administering to said mammal a therapeutically effective amount of a polysaccharide enriched extract of Nerium species containing an immunologically active polysaccharide wherein the active polysaccharide comprises acidic homopolygalacturonans or arabinogalaturonans.

12. The method of claim 11, wherein said Nerium species is *Nerium oleander*.

13. The method of claim 11, wherein said disease is a malignancy.

14. The method of claim 13, wherein said disease is adenocarcinoma.

15. The method of claim 11, wherein said disease is a non-malignancy.

16. The method of claim 15, wherein said non-malignancy is psoriasis.

17. The method of claim 11, wherein said extract inhibits the in vivo growth of syngeneic tumors in mice.

18. The method of claim 11, wherein said extract inhibits the phorbol ester or zymosan induced chemiluminescence of human monocytes, but not human neutrophils in vitro.

19. The method of claim 11, wherein said administration is parenteral.

20. The method of claim 19, wherein said parenteral administration is by subcutaneous, intramuscular, intraperitoneal, intracavity, or intravenous injection, or transdermal, nasopharyngeal, or mucosal absorption.

21. The method of claim 20, wherein said dosage is from about 0.05 ml to about 1.0 ml.

22. The method of claim 20, wherein said dosage is from about 0.2 ml to about 0.9 ml.

23. The method of claim 20, wherein said dosage is from about 0.3 ml to about 0.7 ml.

24. The method of claim 11, wherein said administration is enternal.

25. The method of claim 24, wherein said dosage is from about 0.1 ml to about 2.5 ml.

26. The method of claim 24, wherein said dosage is from about 0.2 ml to about 1.0 ml.

27. The method of claim 24, wherein said dosage is from about 0.3 ml to about 0.7 ml.

* * * * *